US007380942B2

(12) United States Patent
Molebny et al.

(10) Patent No.: US 7,380,942 B2
(45) Date of Patent: Jun. 3, 2008

(54) METHOD FOR MEASURING THE WAVE ABERRATIONS OF THE EYE

(76) Inventors: Sergiy Molebny, 2111 Welch St., Apt. A230, Houston, TX (US) 77019; Vasyl Molebny, Velyka Kytaivska St., 6, Apt. 9, Kiev (UA) 252028; LaMar Frederick Laster, 4377 N. MacGregor Way, Houston, TX (US) 77004

( * ) Notice: Subject to any disclaimer, the term of this patent is extended or adjusted under 35 U.S.C. 154(b) by 346 days.

(21) Appl. No.: 10/530,132

(22) PCT Filed: Oct. 6, 2003

(86) PCT No.: PCT/US03/31610

§ 371 (c)(1),
(2), (4) Date: Apr. 4, 2005

(87) PCT Pub. No.: WO2004/032712

PCT Pub. Date: Apr. 22, 2004

(65) Prior Publication Data

US 2006/0170868 A1    Aug. 3, 2006

(30) Foreign Application Priority Data

Oct. 4, 2002    (UA)    .............................. 2002107925

(51) Int. Cl.
*A61B 3/14* (2006.01)
*A61B 3/00* (2006.01)
(52) U.S. Cl. ...................... 351/246; 351/206
(58) Field of Classification Search ................ 351/246, 351/205–206, 211–216, 200
See application file for complete search history.

(56) References Cited

U.S. PATENT DOCUMENTS 3,290,927 A    12/1966    Gambs    .......................... 73/80

(Continued)

FOREIGN PATENT DOCUMENTS

JP    63242219    10/1988

(Continued)

OTHER PUBLICATIONS

EyeSys 2000 Corneal Analysis System: The Ultimate in Corneal Topography from the Proven Leader (Brochure). Copyright EyeSys Technologies, Inc., 1995.

(Continued)

*Primary Examiner*—Alicia M Harrington
(74) *Attorney, Agent, or Firm*—Benjamin Aaron Adler (57) ABSTRACT

Provided herein are methods for measuring wave aberrations of the eye. Retinal scattered radiation from a probing laser beam is detected, the wave front tilt is measured as first partial derivatives along known coordinates in a discrete set of the pupil points, the wave front is approximated from this data as functions of the pupil coordinates and the wave aberrations of the eye are thereby calculated. Partial derivatives are determined at any pupil point by spline approximation using the values in a discrete number of points in which the wave front tilts are measured. This set of points may be located along concentric circles or along one of the orthogonal axes. The wave front is reconstructed using numerical integration along the radii with the initial integration point in the center of the pupil. Wave aberrations are calculated from wave front data reconstructed in the form of splines.

14 Claims, 9 Drawing Sheets

U.S. PATENT DOCUMENTS

| | | | | |
|---|---|---|---|---|
| 4,190,332 | A | 2/1980 | Body et al. | 351/211 |
| 4,465,348 | A | 8/1984 | Lang et al. | 351/211 |
| 4,691,716 | A | 9/1987 | Tanne | 128/774 |
| 4,778,268 | A | 10/1988 | Randle | 351/203 |
| 4,796,989 | A | 1/1989 | Fukuma et al. | 351/212 |
| 5,148,205 | A | 9/1992 | Guilino et al. | 351/159 |
| 5,258,791 | A | 11/1993 | Penney et al. | 351/211 |
| 5,293,871 | A | 3/1994 | Reinstein et al. | 128/660.06 |
| 5,414,478 | A | 5/1995 | van Gelderen | 351/212 |
| 5,418,714 | A | 5/1995 | Sarver | 364/413.13 |
| 5,581,405 | A | 12/1996 | Meyers et al. | 359/571 |
| 5,589,897 | A | 12/1996 | Sinclair et al. | 351/223 |
| 5,722,427 | A | 3/1998 | Wakil et al. | 128/898 |
| 5,841,511 | A | 11/1998 | D'Souza et al. | 351/212 |
| 5,847,804 | A | 12/1998 | Sarver et al. | 351/206 |
| 5,875,019 | A | 2/1999 | Villani | 351/211 |
| 5,953,100 | A | 9/1999 | Sarver et al. | 351/206 |
| 6,000,800 | A | 12/1999 | Webb et al. | 351/211 |
| 6,004,313 | A | 12/1999 | Shimmick et al. | 606/5 |
| 6,082,856 | A | 7/2000 | Dunn et al. | 351/160 |
| 6,130,419 | A | 10/2000 | Neal | 250/201.9 |
| 6,199,986 | B1 | 3/2001 | Williams et al. | 351/221 |
| 6,234,631 | B1 | 5/2001 | Sarver et al. | 351/212 |
| 6,382,795 | B1 | 5/2002 | Lai | 351/212 |
| 6,382,797 | B1 | 5/2002 | Bille et al. | 351/212 |
| 6,409,345 | B1 | 6/2002 | Molebny et al. | 351/212 |
| 2001/0033362 | A1* | 10/2001 | Sarver | 351/212 |
| 2002/0024643 | A1 | 2/2002 | Nakauchi et al. | |
| 2003/0011745 | A1 | 1/2003 | Molebny et al. | |
| 2003/0078753 | A1 | 4/2003 | Campin et al. | |

FOREIGN PATENT DOCUMENTS

| | | |
|---|---|---|
| UA | 98105286 | 7/1998 |
| WO | PCT/US99/23327 | 7/1999 |

OTHER PUBLICATIONS

Contact Lenses: Update 1—Chapter 4—Corneal Topography by J. James Rowsey and David J. Schanzlin (Copyright 1986 by Little, Brouwn and Company).

Contact Lenses—Chapter 17—Measurement of Corneal Curvature: Keratometer (Ophthalmometer) by Oliver H. Dabezies, Jr. and Jack T. Holladay (Copyright 1984 by Little, Brown and Company.

A Comprehensive Guide to Fitting Contact Lenses with EyeSys Pro-Fit Contact Lens Fitting Software by Beth A. Soper, C.O.A. (EyeSys System 2000—Version 3.1).

Van de Brink. Measurement of the geometrical aberrations of the eye. Vision Res. 2, pp. 233-244, 1962.

N.M. Sergienko. Oftalmologicheskaya optika (Ophtalmic Optics). Moscow, Meditsina, 1991, 142 pages. English translation of: p. 30-32 text of the last paragraph referring to Figure 19 continuing onto pp. 31 and 32, and first full paragraph of p. 32.

R.H. Webb, C.M. Penney, and K.D. Thompson. Measurement of ocular local wavefront distortion with a spatially resolved refractometer. Applied Optics. 31, pp. 3678-3686, 1992.

S.G. El Hage and Bemi F. Contribution of the crystalline lens to the spherical aberration of the eye. J. Opt. Soc. Am. 63, pp. 205-211, 1973.

J. Liang, B. Grimm, S. Goelz, and J. F. Bille, Objective measurement of wave aberrations of the human eye with the use of a Hartmann-Shack wave-front sensor. J Opt. Soc. A. A 11,pp. 1949-1957, 1994.

J. Liang and D.R. Williams. Aberrations and retinal image quality of the normal human eye. J Opt. Soc. Am. A 14, pp. 2873-2883, 1997.

J. Liang, D.R. Williams and D.T. Miller. Supernormal vision and high resolution retinal imaging through adaptive optics, J. Opt. Soc. Am., A 14, pp. 2884-2892, 1997.

T. Seiler, P.J. McDonnell, "Excimer laser photorefractive keratectomy", Surv. of Ophthalm., 40, pp. 89-118, 1995.

Eye Sys Technologies brochure. EyeSys Software The power that drives high performance corneal topography. EyeSys Technologies Inc., 1995.

W.D. West, OD. Corneal Topography: It's not just for surgeons anymore. Eyecare Technology, Jul./Aug. 1995.

* cited by examiner

Fig. 17 ated wave front, the partial derivatives at any pupil point are determined by means of spline approximation using the values in a discrete set of points, where the wave front tilts are measured, and the wave front is reconstructed by means of the numerical integration along the radii with the initial point of integration located in the center of the pupil, where identical initial values of the integral are taken for all radii.
METHOD FOR MEASURING THE WAVE ABERRATIONS OF THE EYE

BACKGROUND OF THE INVENTION

The invention relates to medical instrumentation, in particular to diagnostic measuring devices, and can be applied, for example, for high-accuracy vision correction.

Methods are known for measuring the wave aberrations of the optical system of the human eye as a function of spatial pupil coordinates. Said methods use probing the eye with a thin laser beam, its backscattering by the retina, detection of the component exiting from the eye by means of photosensitive devices, and measurement of the wave front tilt in different pupil points with known coordinates. These data are used for the wave front approximation and calculation of the wave aberration of the eye as wave front deformations.

Some methods use measurement of the wave front structure at the exit of the eye simultaneously in time by means of partitioning this structure into subapertures (D. R. Williams, et al. Rapid, automatic measurement of the eye's wave aberrations. U.S. Pat. No. 6,199,986. Int. Cl. A61B 3/10, 13.03.2001). Subapertures are formed using a matrix of coaxial lenses and a matrix of position sensing photodetectors installed in their foci. The wave front is reconstructed from the measured set of tilts simultaneously in all subapertures.

Ray tracing method for measuring the wave front and refraction aberrations successively in time (V. V. Molebny, et al. Device for measuring refraction aberrations of the eye. (Ukrainian Patent Application No. 98105286, now Patent No. 46833, Int. Cl. A61B 3/00, A61B 3/10, A61B 3/14, filed Oct. 7, 1998), is also known. According to this method, the eye is probed by a thin laser beam (its cross-section at the eye entrance is 0.2-0.3 mm), shifted in parallel to itself over the entrance aperture of the eye successively in time, the coordinates of the points on the retina, to which the laser beam is projected, are measured at each probing. Said data obtained in a discrete set of points of the eye aperture are used to calculate the wave front tilt in these points and then approximate the entire wave front surface.

Both of the above mentioned methods use the approximation of the wave front using a series of Zernike polynomials. The use of said series results in some restrictions, which lead to non-uniform spatial resolution when describing the refraction non-homogeneity over the eye aperture. Thus, in the central zone, which is the most significant for the acuity of vision, spatial resolution is lower than in the peripheral zone if describing the refraction non-homogeneity by means of Zernike polynomials.

To obtain a higher spatial resolution in the center, the number of polynomials must be increased, therefore, measurements in the larger number of aperture points are required, not only in the center but also at the periphery, making the procedure of measurement more complicated: radiation exposure of the eye is increased, calculation process becomes significantly longer and more complicated (the number of equations increases to a few hundreds).

Both above mentioned methods are equivalent from the point of view of wave front approximation using the series of Zernike polynomials. Each method can be regarded as a prototype. Let us take the ray tracing principle for a prototype.

SUMMARY OF THE INVENTION

A goal of this invention is formulated as uniformly increasing the spatial resolution of the measurement of the refraction non-homogeneity over the entire aperture of the eye not entering into a complicated embodiment of said method that could disproportionately increase the number of probing points in the peripheral zone, increase the time of measurement, as well as increase the radiation dose of the patient's eye.

The formulated goal is achieved in such a way that in the method based on the probing the eye with a thin laser beam, on the detection of the radiation scattered by the retina, on the measurement of the wave front tilt in the form of the first partial derivatives along the coordinates in a discrete set of pupil points with known coordinates, on the approximation of the wave front in the form of functions of pupil coordinates using said data, and on the calculation of wave aberrations of the eye as deformations of approximated wave front, the partial derivatives at any pupil point are determined by means of spline approximation using the values in a discrete set of points, where the wave front tilts are measured, and the wave front is reconstructed by means of the numerical integration along the radii with the initial point of integration located in the center of the pupil, where identical initial values of the integral are taken for all radii.

Furthermore, a discrete set of points, in which the wave front tilt is measured, is located along concentric circles with the common center, which coincides with the center of coordinates.

Furthermore, the approximation of partial derivatives at the beginning is performed along each concentric circle, and then—along the radii.

In another version, a discrete set of points, at which the wave front tilt is measured, is located along straight lines which are parallel to one of the axes of the rectangular system of coordinates.

Approximation of the partial derivatives is performed along each of the parallel lines and then—in orthogonal directions.

In addition, in still another embodiment of the proposed method, spline approximation along each coordinate is performed in accordance with the formula:

$$S(x) = \frac{(x_{i+1} - x)^2[2(x - x_i) + (x_{i+1} - x_i)]}{(x_{i+1} - x_i)^3} S(x_i) +$$

$$\frac{(x - x_i)^2[2(x_{i+1} - x) + (x_{i+1} - x_i)]}{(x_{i+1} - x_i)^3} S(x_{i+1}) +$$

$$\frac{(x_{i+1} - x)^2(x - x_i)}{(x_{i+1} - x_i)^2} S'(x_i) - \frac{(x - x_i)^2(x_{i+1} - x)}{(x_{i+1} - x_i)^2} S'(x_{i+1}),$$

where $S(x)$ is the interpolation cubic spline along the generalized coordinate x; $x_i$, $x_{i+1}$ are the coordinates of the pupil points i and (i+1) from their discrete set, at which the wave front tilt is measured having the corresponding values $S(x_i)$, $S(x_{i+1})$; and $S'(x_i)$, $S'(x_{i+1})$ are the values of the first derivative in the points $x_i$, $x_{i+1}$, which ensure the continuity of the second derivative $S''(x)$ in these points.

Furthermore, numerical integration is proposed to be performed in accordance with the formula:

$$W(P, \Phi) = W(0, \Phi) + \int_0^P \frac{\partial W(\rho, \Phi)}{\partial \rho} d\rho,$$

where $W(\rho,\phi)$ is the wave front function, $\rho$—the coordinate along the radius, $\phi$—the coordinate along the angle, $(P, \Phi)$ are the coordinates of the arbitrary pupil point, and $$\int_0^P \frac{\partial W(\rho, \Phi)}{\partial \rho} d\rho \approx \sum_{i=1}^N \frac{\partial W\left(\frac{\rho_{i-1} + \rho_i}{2}, \Phi\right)}{\partial \rho} (\rho_i - \rho_{i-1}),$$

the interval $[0,P]$ being divided into N partial portions $[\rho_{i-1},\rho_i]$, so that $i=\overline{1,N}$.

Spatial resolution in the central zone is increased in the proposed method by using the wave front approximation uniform on the entire eye without the complication of the measurement procedure as well as without the increase of the eye irradiation dose.

Allocation of a discrete set of points along concentric circles with the common center, which coincides with the center of coordinates, helps to simplify the process of approximation of the partial derivatives (at the beginning, along each circle and then—along the radii).

In still another version of the embodiment, the process of approximation of partial derivatives is simplified due to the allocation of a discrete set of points along straight lines which are parallel to one of the axes of the rectangular system of coordinates and by performing the approximation of partial derivatives at the beginning along each of the parallel lines and then—in orthogonal directions.

Uniformity of spatial resolution over the entire aperture is ensured by using the interpolation cubic spline $S(x)$ in accordance with the above mentioned mathematical formula and under the condition of continuity of its second derivative $S''(x)$ in the subaperture points, where the wave front tilt is measured.

Important peculiarity of the proposed method is also the procedure of numerical integration while reconstructing the wave front in accordance with the above mentioned mathematical formula along the radii from the center of the pupil in such a way that the initial value of integral is the same for all radii. It essentially facilitates the problem of the correctness of the results in the central zone, occurred if using the approximation by means of Zernike polynomials.

BRIEF DESCRIPTION OF THE DRAWINGS

The subject matter of the invention is illustrated by drawings including 17 figures.

Let us discuss in detail implementation of the proposed method for measuring the wave aberrations of the human eye.

Figure 1:
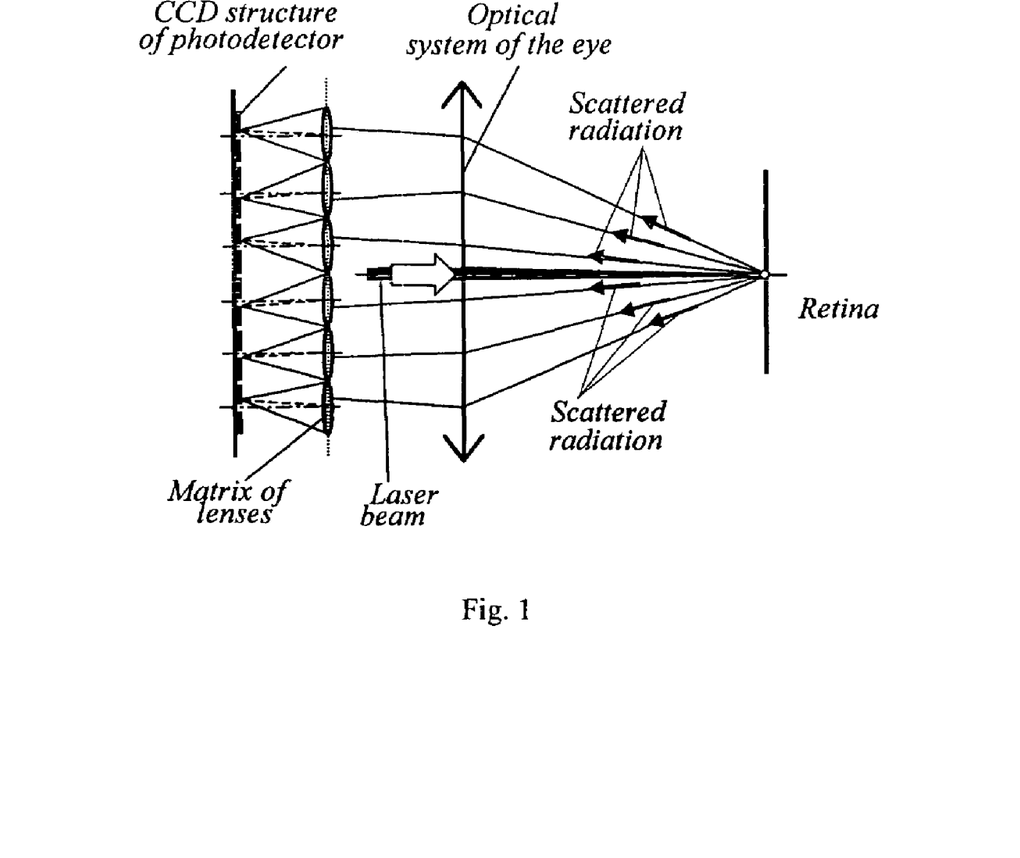
FIG. 1. Course of rays in the device for measuring aberrations using Hartmann-Shack sensors.

FIG. 1 explains the concept of measurement of the wave aberrations of the eye using Hartmann-Shack sensor. The optical system of the eye is represented in this figure as a thin lens and the retina is placed in the focus of this lens. A thin parallel laser beam is directed into the eye. Preferably the beam enters the central zone of the pupil so that its axis coincides with the visual axis of the eye (for simplicity, physiological peculiarities of the vision are not taken into account, according to which, visual and optical axes are to be differentiated—we shall use these terms as synonyms). The optical system of the eye focuses the laser beam into the point whose size is determined in an ideal case only by the refraction.

This illuminated point acts as a secondary point irradiator whose light is scattered in a certain spatial angle and a part of it is propagating through the eye pupil. A matrix (raster) of coaxial lenses with diameter approximately 0.3-1.0 mm (sometimes even less) is installed on the path of radiation. These lenses have identical focal lengths. System of position sensing photodetectors is installed in the foci of the lenses. It is common to use a TV matrix of charge-coupled devices (CCD).

Coordinates of each illuminated point are measured in foci of microlenses. Deviation of the illuminated point from the optical axis of a corresponding lens is the measure of the deviation of the wave front in the zone of this lens (in the subapertute of the wave front), being (in linear approximation) the first partial derivative along the coordinates for this wave front subaperture. Based on these data (deviation and coordinates), the wave front is approximated as functions of pupil coordinates and then aberrations of the wave front are calculated as its deformations.

Ray tracing method differs in several details, but the sequence of procedures is the same as with Hartmann-Shack sensors. The main difference is successive (in time) measurement of the wave front tilts in its subapertures.

Figure 2:
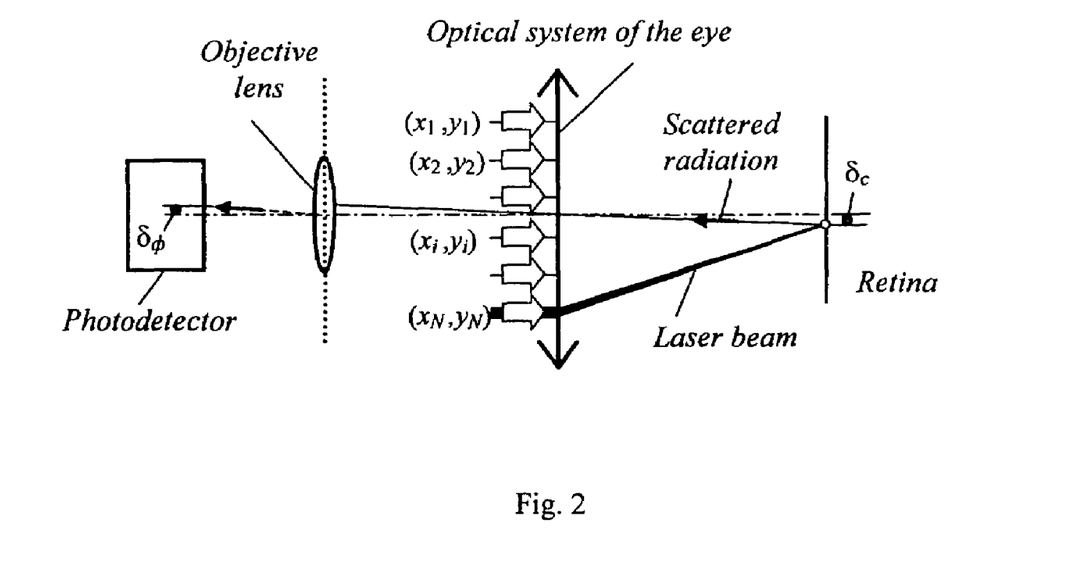
FIG. 2. Course of rays in the ray tracing device for measuring aberration in successive moments of time.

FIG. 2 shows the course of rays in the ray tracing procedure in successive moments of time. In this figure, the optical system of the eye is shown as a thin lens, the retina being located in its focus. In the first moment, a thin laser beam is directed into the eye at the pupil point with coordinates $(x_1,y_1)$. In the next moment, said beam is directed to a point with the coordinates $(x_2,y_2)$. The procedure continues in this manner up to the last point of the eye aperture with the coordinates $(x_N,y_N)$. Each time, the laser beam is projected on the retina as a point (a point is an abstraction, actually, it is a more sophisticated figure, though roughly speaking it may be considered as a point).

Like in the above case, this point is a secondary point irradiator, and it is possible to detect it by means of a photodetector with an objective lens. Also, it is a position sensing photodetector generating at its output the coordinates of the image of the retinal point, into which the laser beam is projected after having entered the eye pupil with the known coordinates $(x_i, y_i)$.

Deviation of the laser beam projection $\delta_c$ on the retina is unambiguously related to the measured deviation $\delta_\varphi$ in the plane of photodetector. This value is the measure of beam deviation or adequately the measure of wave front deviation at the point of eye aperture with known coordinates. Thus, like in the first method, as a result of performed measurements, a wave front tilt is obtained in the points of eye aperture with the known coordinates.

Based on these data (like in the first method, this is the tilt and the coordinates), the wave front is approximated as functions of pupil coordinates, and then aberrations of the wave front are calculated as its deformations.

Figure 3:
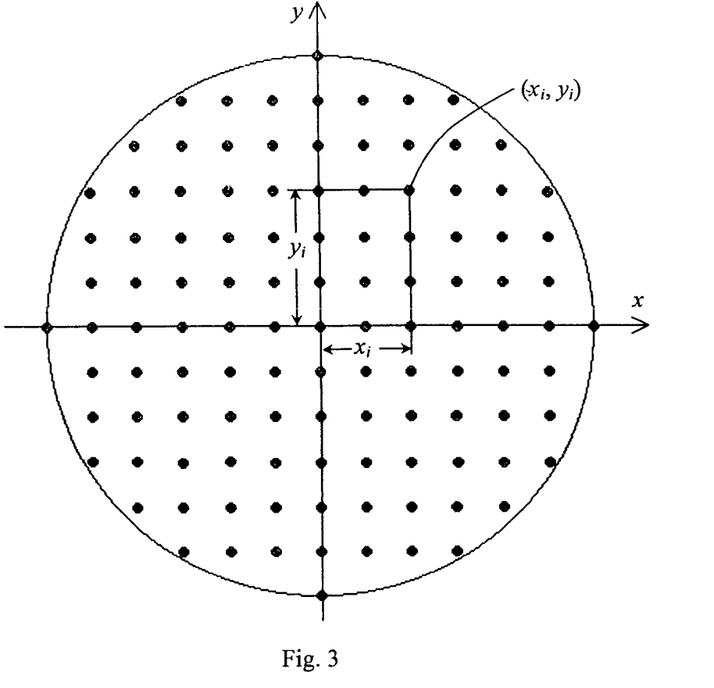
FIG. 3. Set of points for measuring the wave front tilt located on straight lines parallel at least to one of the axes of coordinates.
Figure 4:
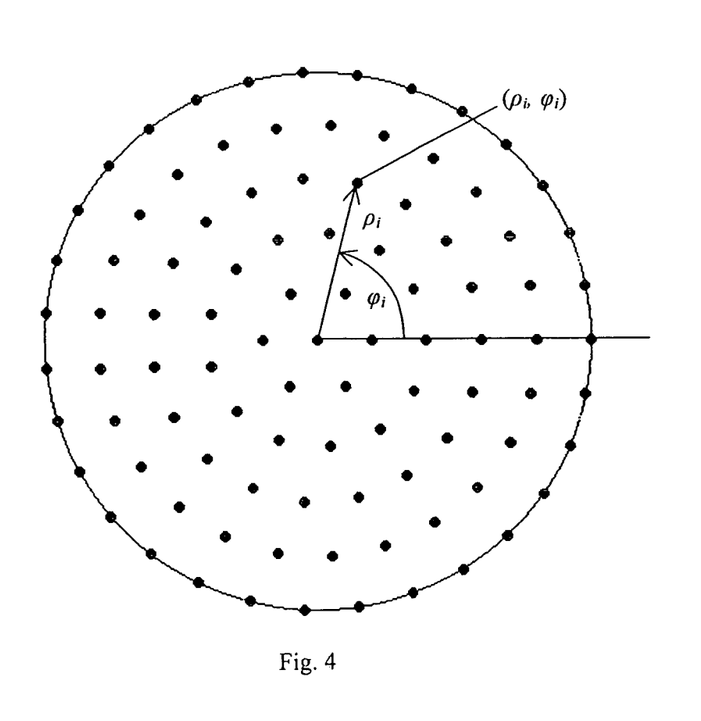
FIG. 4. Set of points for measuring the wave front tilt located on concentric circles.

FIGS. 3 and 4 depict the disposition of the set of points on the eye aperture, where the wave front tilt is measured, the points of the set in FIG. 3 being located along straight lines in parallel to the axes of the Cartesian system of coordinates. Their coordinates $(x_i,y_i)$ are also represented in the rectangular system of coordinates. In FIG. 4, these points are located along the concentric circles. It is convenient to describe their coordinates in the polar system of coordinates $(\rho_i,\varphi_i)$.

As a rule, the rectangular system of coordinates is used in the method based on Hartmann-Shack sensor (FIG. 3), and the polar system of coordinate, more appropriate for a natural round eye aperture, is used in the ray tracing method (FIG. 4). The use of one or another system of coordinates in the proposed method affects only the procedure of calculation of the approximation functions.

Figure 5:
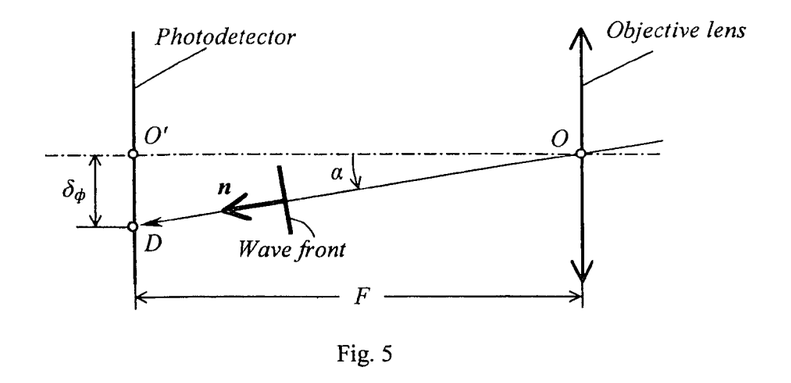
FIG. 5. Measurement of the wave front tilt using the coordinates of the laser beam projection on the photodetector.

FIG. 5 shows the relation between the measured value $\delta_\varphi$ of the shift of the laser beam projection in a subaperture (Hartmann-Shack sensor method) or in the entire aperture (ray tracing method). The wave front tilt can be described by an angle $\alpha$ or by a unit vector n normal to the wave front surface. The angle $\alpha$ is determined from the relation for a triangle ODO':

$$tg\alpha = \frac{O'D}{OO'},$$

where $O'D=\delta_\varphi$ is the measured value of the shift of the laser beam projection in the photodetector plane, and $OO'=F$–the focal length of the objective lens. One gets from this expression:

$$\alpha = \text{arc}tg\frac{\delta_\varphi}{F}.$$

Figure 6:
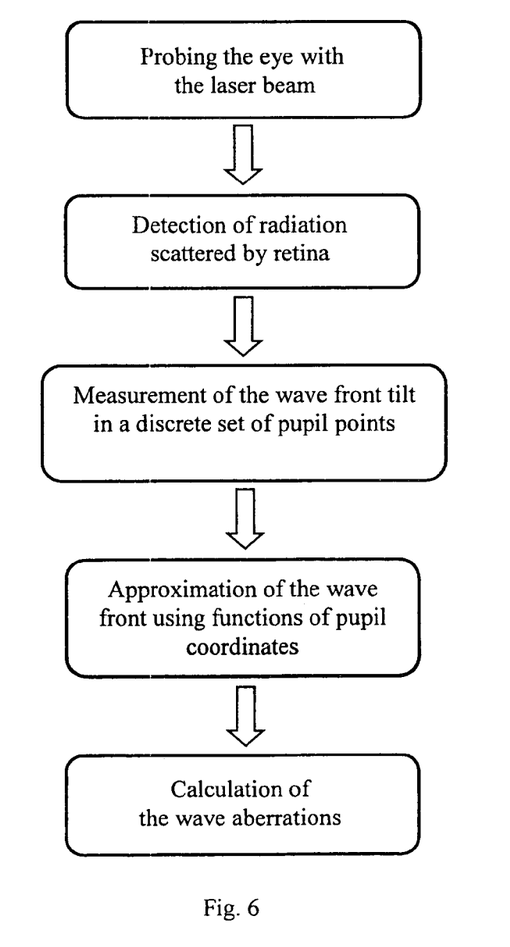
FIG. 6. Sequence of procedures while measuring the wave aberrations of the eye.

The sequence of the procedures in the course of measurement of wave aberrations is illustrated in FIG. 6. This sequence comprises the following steps:

(a) probing the eye with the laser beam;

(b) detection of the radiation scattered by the retina;

(c) measurement of the wave front tilt in a discrete set of pupil points;

(d) approximation of the wave front with the functions of pupil coordinates;

(e) calculation of wave aberrations.

Figure 7:
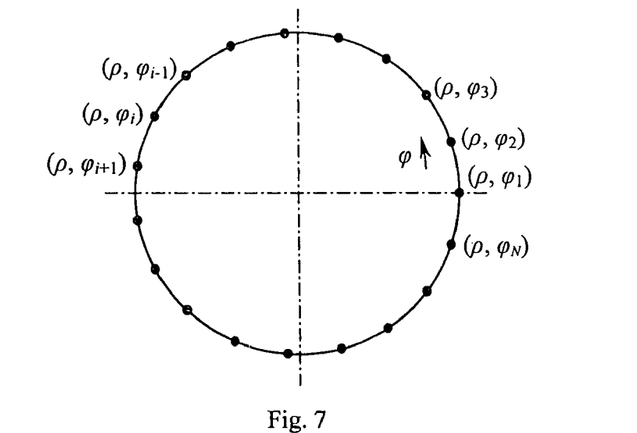
FIG. 7. Circular trajectory of approximation.
Figure 8:
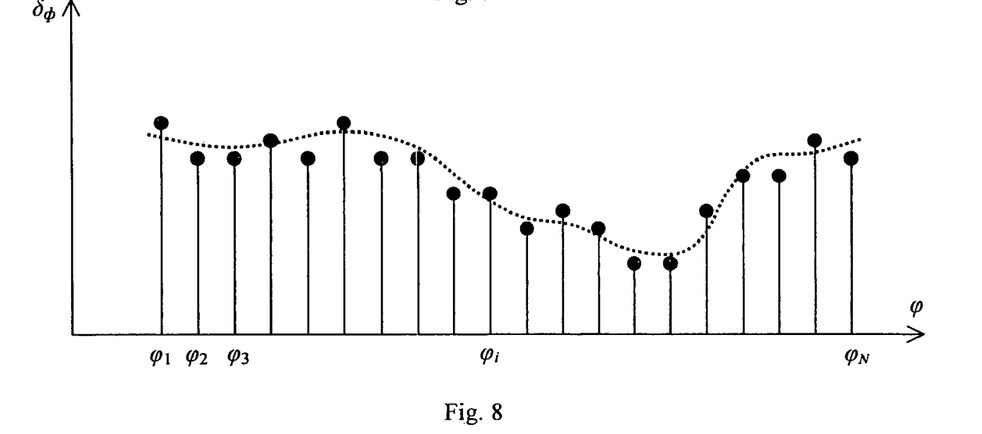
FIG. 8. Approximation result (broken curve) along the circular trajectory by means of the least squares method.

In the prototype method in order to approximate the wave front, series of Zernike polynomials are used. The solution of the problem is assisted by the least squares method. This procedure is schematically illustrated in FIGS. 7 and 8. A circular trajectory of scanning, which means the trajectory of constant radius $\rho$, is shown in FIG. 7. This trajectory includes fixed points with known coordinates $(\rho,\varphi_1)$, $(\rho,\varphi_2), \ldots, (\rho, \varphi_i), \ldots, (\rho, \varphi_N)$, in which the value $\delta_\varphi$ is measured.

Diagram of values $\delta_\varphi$ for points from $\varphi_1$ to $\varphi_N$ is shown in FIG. 8. A module of this value is shown in the diagram, its orthogonal components being analyzed in the analytical record. A continuous function (series of polynomials) is illustrated in FIG. 8 by dotted line which, by means of the least squares method, approximates the trajectory of beam projection on the photodetector (for the ray tracing method). As one can see, the approximation function takes the values differing from the measured values. This is one of the sources of the error of measurement. Another source results from the use of Zernike polynomials leading to a non-uniform spatial resolution when describing refraction non-homogeneity in the eye aperture, whereas in the central zone the spatial resolution of measurements is lower than in the peripheral zone, that reduces the valuables of the obtained information on eye aberrations since this central zone is the most significant for the acuity of vision.

A higher spatial resolution can be reached by increasing the number of measuring points, allowing a larger number of approximating terms of the series. This will usually lead to more complicated measurements and will increase the dose of retina irradiation. The calculation process also becomes more complicated and longer due to necessary increase of the number of equations.

Figure 9:
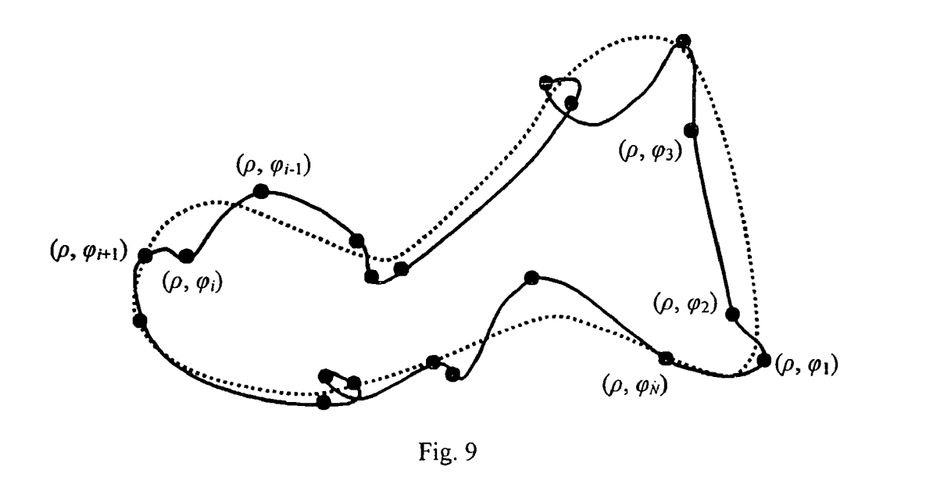
FIG. 9. Retinal spot diagram (for the ray tracing method with the trajectory, shown in FIG. 7) after approximation by means of the least squares method (Zernike polynomials are used)—broken curve; and after approximation using bicubic splines—continuous curve.

Spline approximation is used in the proposed method, according to which, the trajectory of beam projection on the retina is not approximated by means of the least squares method (broken trajectory FIG. 9), but passes through the measured values of beam deviation for probing points with coordinates $(\rho,\varphi_1), (\rho,\varphi_2), \ldots (\rho,\varphi_i), \ldots, (\rho,\varphi_N)$.

Figure 10:
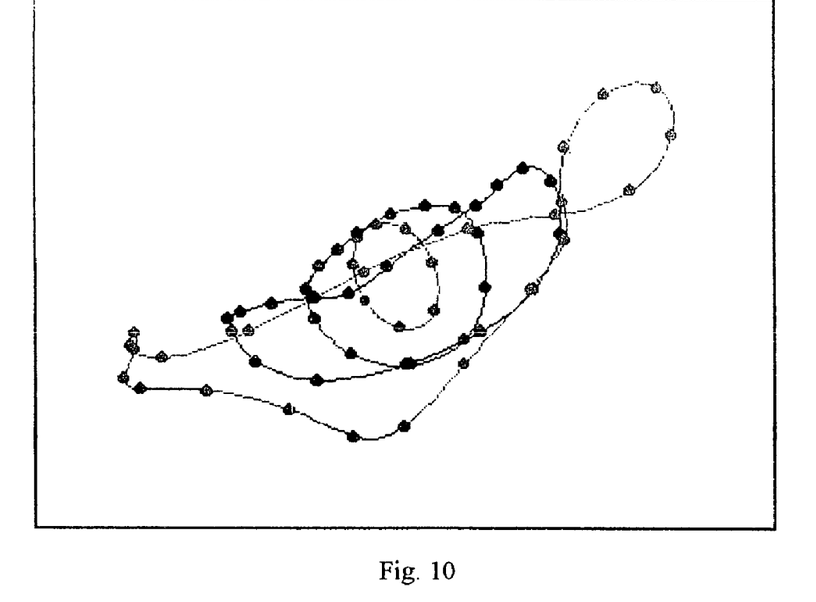
FIG. 10. Retinal spot diagram (for the ray tracing method with four circular trajectories at the entrance aperture of the eye) after approximation by means of the least squares method (using Zernike polynomials).
Figure 11:
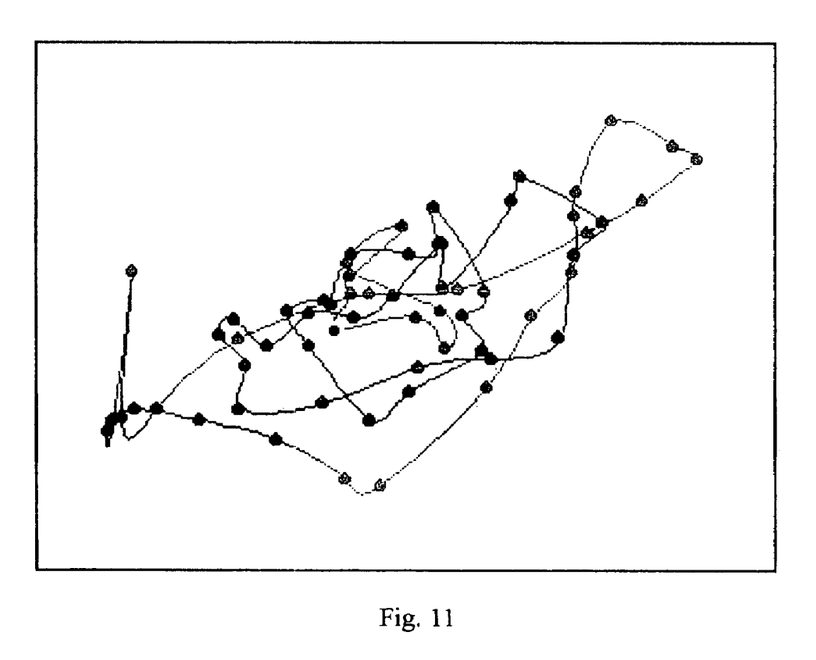
FIG. 11. Retinal spot diagram (for ray tracing method with four circular trajectories at the entrance aperture of the eye) after approximation using bicubic splines (for the same initial data as shown in FIG. 10).

FIGS. 10 and 11 are examples of trajectory of beam projection on the retina (retinal spot diagram) approximated using the same measurement data: by means of the least squares method in FIG. 10, and by means of splines in FIG. 11. Flatness of the approximated trajectories in FIG. 10 is obviously more distinct than in FIG. 11, that certifies the loss of considerable part of information on variations of the refraction non-homogeneity containing the higher spatial frequencies.

Figure 12:
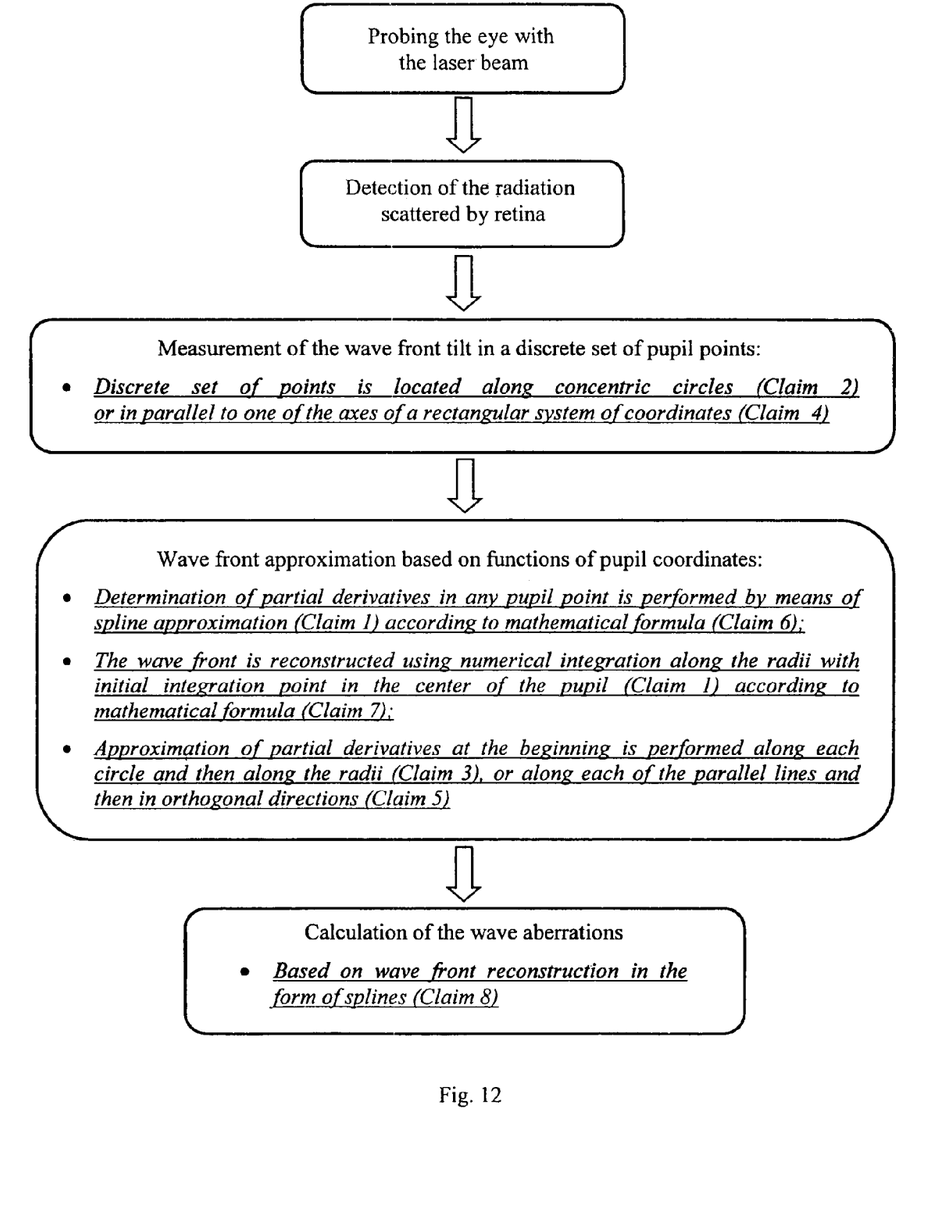
FIG. 12. Sequence of procedures while measuring the wave aberrations of the eye using the proposed method.

The proposed method for measurement of wave aberration of the eye differs from its prototype due to inclusion of some distinctive features (as illustrated in FIG. 12) into the procedures shown in FIG. 6, which are essential for the proposed method. Let us discuss aforementioned distinctions in the sequence of their use referencing to the corresponding claims.

In the procedure of measurement of the wave front tilt in a discrete set of the pupil points, this set of points is formed either along concentric circles (as provided in claim 2) or in parallel to one of the axes of the rectangular coordinate system (claim 4).

The wave front approximation using functions of pupil coordinates includes the following distinctive features:

(a) Partial derivatives in any point of the pupil are determined using spline approximation (claim 1). According to the claim 6, this approximation is performed according to the relation, in which the interpolation cubic spline $S(x)$ along the generalized coordinate x is derived from the data on the coordinates $x_i$, $x_{i+1}$ of the pupil points i and (i+1) from their discrete set, in which the wave front is measured, and from the data on the values of the first derivative $S'(x_i)$, $S'(x_{i+1})$ in the points $x_i$, $x_{i+1}$. The condition of continuity of its second derivative $S''(x)$ in these points must be satisfied.

(b) Wave front is reconstructed by means of the numerical integration along the radii with the initial integration point in the pupil center (claim 1). The claim 7 specifies this procedure by means of mathematical relation for the wave front $W(P,\Phi)$ in any point of the pupil using known values of derivatives $$\frac{\partial W(\rho, \Phi)}{\partial \rho}$$

in the polar system of coordinates $(\rho,\phi)$.

The interval of integration [0,P] is divided here into N partial portions $[\rho_{i-1},\rho_i]$ so that $$i = \overline{1, N},$$

and the intergal $$\int_0^P \frac{\partial W(\rho, \Phi)}{\partial \rho} d\rho$$

is replaced by a sum $$\sum_{i=1}^N \frac{\partial W\left(\frac{\rho_{i-1}+\rho_i}{2}, \Phi\right)}{\partial \rho}(\rho_i - \rho_{i-1}).$$

(c) Approximation of partial derivatives, at the beginning, is performed along each circle and then—along the radii (claim 3). In another embodiment of this method, the approximation is performed along each of the parallel straight lines and then—in orthogonal directions (claim 5).

In the process of calculation of wave aberrations, an essential distinctive feature is also included: wave aberrations, for example, in the form of a series of Zernike polynomials are now calculated not from a limited set of data including only the discrete points, in which the measurement was taken, but the continuous functions. Thus, for calculation of any number of the terms of a Zernike series, there is no need in increasing the number of measuring points, since the wave front surface is described by splines complying with the continuity conditions.

Figure 13:
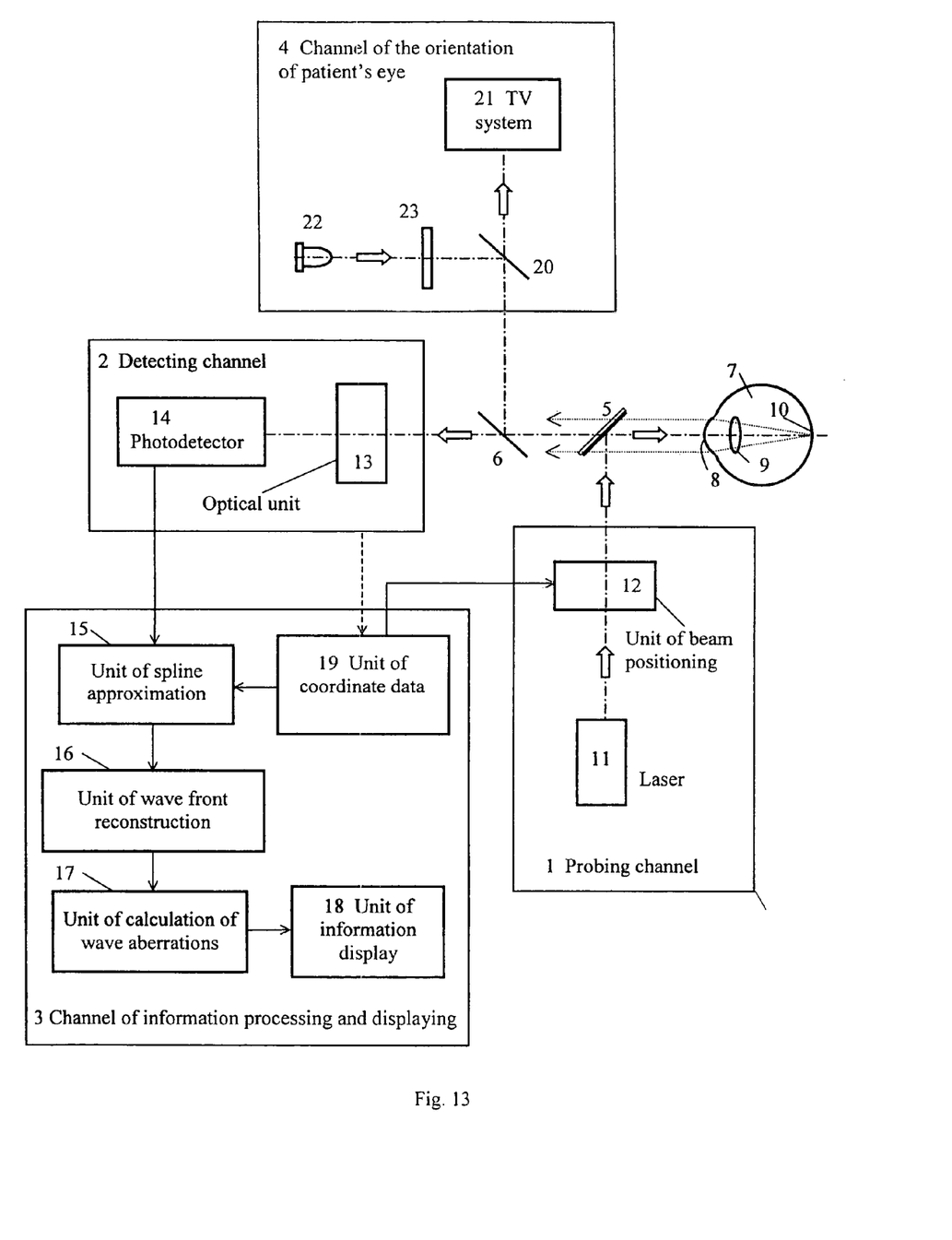
FIG. 13. Functional schematic diagram of a device for measurement of the wave aberrations of the eye using the proposed method.

A functional schematic diagram of the device for measurement of wave aberrations of the eye based on this method is shown in FIG. 13. It comprises: a probing channel 1, a detecting channel 2, a channel 3 of information processing and displaying, a channel 4 of orientation of the patient's eye, and a polarization beam splitter 5 installed at the exit of the probing channel 1, and a first beam splitter 6 installed in front of said detecting channel 2 and said channel 4 of orientation of patient's eye. An eye under investigation 7 comprises a cornea 8, a crystalline lens 9, and a retina 10.

Said probing channel 1 consists of successively installed laser 11 and a unit of beam positioning 12. Said detecting channel 2 includes successively installed an optical unit 13 and a photodetector 14.

Said channel 3 of information processing and displaying is made of a unit 15 of spline approximation, a unit 16 of wave front reconstruction, a unit 17 of calculation of wave front aberrations, a unit 18 of information display, and a unit 19 of coordinate data.

The input of said unit 15 of spline approximation is connected to the output of said photodetector 14. The units 15, 16, 17 and 18 are connected in such a way that the input of each next unit is connected to the output of the previous one. The output of said unit 19 of coordinate data is connected to said unit 12 of beam positioning and the input of said unit 15 of spline approximation.

Said channel 4 of orientation of patient's eye consists of a second beam splitter 20, a TV camera 21, a light source 22 and an accommodation transparency 23, here the elements 22, 23 are installed successively, and the radiation of the light source is directed into the patient's eye so that it is reflected twice: by said second beam splitter 20 and by said first beam splitter 6, and passes through said polarization beam splitter 5.

Functioning of the device. Before measurement, said patient's eye 7 is to be oriented so that its line of sight coincides with the optical axis of the device. For this purpose, the patient has to direct his/her sight onto the light source 22 which is made of a light source itself which can be, for example, a light emitting diode (LED), and oi an optical forming system. When using this system, the accommodation transparency 23 can be conjugated with the retina of the eye in a wide range of distances (for the sake of simplicity, these elements are not shown in FIG. 13). Said TV system 21 ensures the visualization of the orientation process. This process is important for obtaining correct results of measurements but not essential for showing distinctive features of the proposed method.

In the moment when the patient's eye is correctly oriented and accommodated to the target distance, the laser 11 is switched on. Laser radiation is stepwise shifted all over the pupil as shown in FIGS. 2 and 4. After passing through the refracting surfaces and eye structures 7, this radiation hits the retina. Radiation of the laser 11 is linearly polarized. As a result of scattering in the retinal structures, this radiation is depolarized and only the cross component passes through the polarization beam splitter 5 on the way back to the detecting channel 2.

A part of laser radiation reflected by the corneal surface 8 does not pass through the polarization beam splitter 5 (it is well known that the linear polarization is not changed after such reflection). Therefore, only the cross component of radiation scattered by the retina 10 reaches the photodetector.

The plane of the retina 10 and the plane of the photodetector 14 are conjugated by means of said optical unit 13. The measured values of deviations $\delta_\varphi$ (FIGS. 2 and 5) are sent to said unit 15 of spline approximation. Actually, the unit 19 of coordinate data is the driver of said unit 12 of beam positioning which controls the spatial position of the laser beam that enters the eye in parallel to the optical axis of the device. Besides, the data on the coordinates of the pupil points in which the wave front tilt (partial derivatives) is measured in this moment, are transmitted from said unit 19 of coordinate data to said unit 15 of spline approximation. The functions of pupil coordinates, approximating the values of the partial derivatives (unambiguously defined from the deviations $\delta_\varphi$) in any point of the pupil, are reconstructed in said unit 15.

Said unit 16 of wave front reconstruction performs its function using numerical integration along the radii with the initial integration point in the center of the pupil, where the identical initial values of the integral are defined for all radii.

Said unit 17 of calculation of wave front aberrations analyses the deviations of the wave front from an ideal form, and the map (two-dimensional distribution) of said deviations is visualized by said unit 18 of information display.

The structure of the above described device and interaction of its main components are based on the ray tracing method. The structure of a device according to the method which uses the partitioning of the radiation, exiting from the eye, into subapertures, would be in general the same, only said optical unit 13 should perform functions of Hartmann-Shack sensor. Said unit 12 of beam positioning would perform the functions of beam shaping, and the information on the coordinates of the subapertures for said unit 19 of coordinate data should be formed outside of said unit in the detecting channel 2.

Any modification declared in the dependent claims can be implemented using the described device.

For example, said unit 12 of beam positioning performs the function of allocation of a discrete set of points, at which the wave front tilt is measured, along the concentric circles (see FIG. 4) with the common center, which coincides with the center of coordinates (claim 2). Spline approximation of partial derivatives at the beginning is performed along the concentric circles using said unit 15, and then—along the radii (claim 3).

When implementing the proposed method with the Hartmann-Shack sensor, a discrete set of points to measure the tilt of the wave front is located along the straight lines (see FIG. 3), being parallel to one of the axes of the rectangular system of coordinates. Such positioning, as a rule, corresponds to the structure of the matrix raster of said optical unit 13. This structure of a set of the points ensures said unit 15 of spline approximation to perform the approximation of the partial derivatives along each of the parallel lines—at the beginning, and after that—in orthogonal directions (claim 5).

It is necessary to stress, that the straight structure of a set of points can also be realized in the ray tracing method but the circular structure is more rational for it.

Spline approximation along each coordinate is performed using said unit 15 in accordance with the formula:

$$S(x) = \frac{(x_{i+1}-x)^2[2(x-x_i)+(x_{i+1}-x_i)]}{(x_{i+1}-x_i)^3}S(x_i) +$$

$$\frac{(x-x_i)^2[2(x_{i+1}-x)+(x_{i+1}-x_i)]}{(x_{i+1}-x_i)^3}S(x_{i+1}) +$$

$$\frac{(x_{i+1}-x)^2(x-x_i)}{(x_{i+1}-x_i)^2}S'(x_i) - \frac{(x-x_i)^2(x_{i+1}-x)}{(x_{i+1}-x_i)^2}S'(x_{i+1}),$$

where $S(x)$ is the interpolation cubic spline along the generalized coordinate x; $x_i$, $x_{i+1}$ are the coordinates of the pupil points i and (i+1) from their discrete set, in which the wave front tilt is measured having corresponding values $S(x_i)$, $S(x_{i+1})$; and $S'(x_i)$, $S'(x_{i+1})$ are the values of the first derivative in the points $x_i$, $x_{i+1}$, which ensure continuity of the second derivative $S''(x)$ in these points (claim 6).

Wave front reconstruction using said unit 16 can be performed by means of numerical integration in accordance with the formula:

$$W(P,\Phi) = W(0,\Phi) + \int_0^P \frac{\partial W(\rho,\Phi)}{\partial \rho}d\rho,$$

where $W(\rho,\phi)$ is the wave front function, $\rho$—the coordinate along the radius, $\phi$—the coordinate along the angle, $(P,\Phi)$ are the coordinates of an arbitrary pupil point, and $$\int_0^P \frac{\partial W(\rho,\Phi)}{\partial \rho}d\rho \approx \sum_{i=1}^N \frac{\partial W\left(\frac{\rho_{i-1}+\rho_i}{2},\Phi\right)}{\partial \rho}(\rho_i - \rho_{i-1}),$$

the interval [0,P] being divided into N partial portions $[\rho_{i-1},\rho_i]$ so that $i=\overline{1,N}$ (claim 7).

Finally, said unit 17 of calculation of wave aberrations can calculate the wave aberrations not from the data for limited number of points of the pupil, at which the wave front tilts are measured, but from the wave front data reconstructed in the form of splines. That is why there is no need in increasing the number of probing points and consequently in increasing the radiation exposure of the patient's eye, that ensures indisputable advantage of the proposed method together with the increase of the spatial resolution of the measurement of the wave aberrations.

Figure 14:
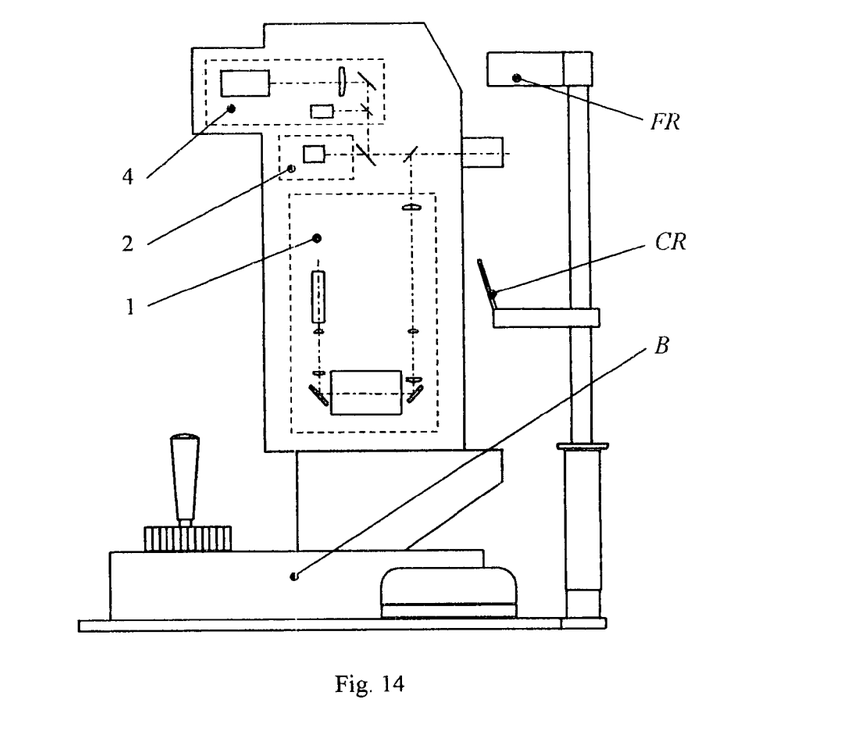
FIG. 14. Schematic design of the optical block of device for measuring the wave aberrations of the eye using the proposed method.

FIG. 14 illustrates an example of a construction of said channels 1, 2 and 4 of the device, implementing the proposed method. All components of the above mentioned channels are installed on a rigid plate fixed to a movable base B of a slit-lamp. Patient has to take place to the right side of the construction having a chin rest CR and a forehead rest FR, to which the patient presses his chin and his forehead.

The construction has three degrees of freedom: up-down, left-right, and forward-backward. Movements and turnings of the patient's head help to reach the coincidence of the optical axis of the device with the line of sight of the eye under investigation, and then the measurements are made. A complete cycle of probing the eye in a complete set of the probing points lasts few tens of milliseconds.

Figure 15:
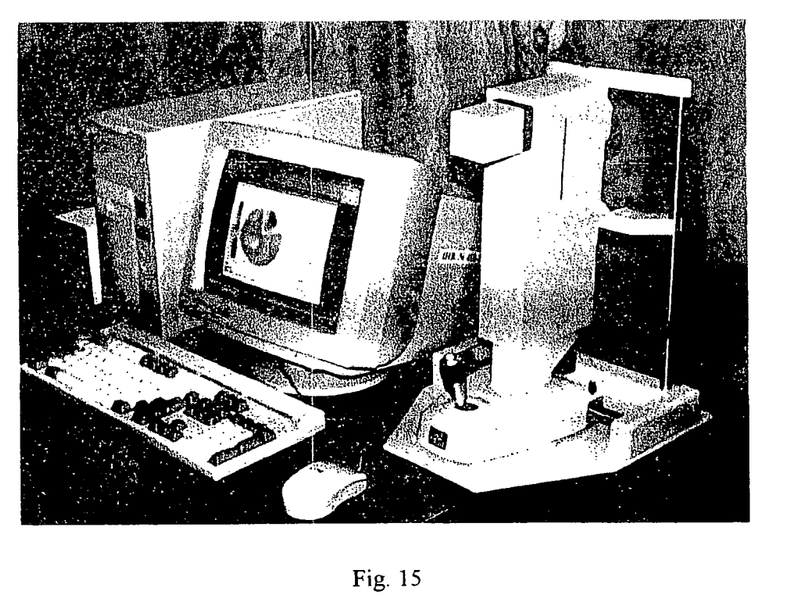
FIG. 15. General view of a device for measuring the wave aberrations of the eye using the proposed method.

A general view of the device is shown in FIG. 15. Besides the slit-lamp base (FIG. 14), the device also comprises a PC-based channel of information processing and displaying. Not only the wave front map but also additional information can be demonstrated on the PC display, this information can be overlaid/combined with the output information from the TV system 21.

Figure 16:
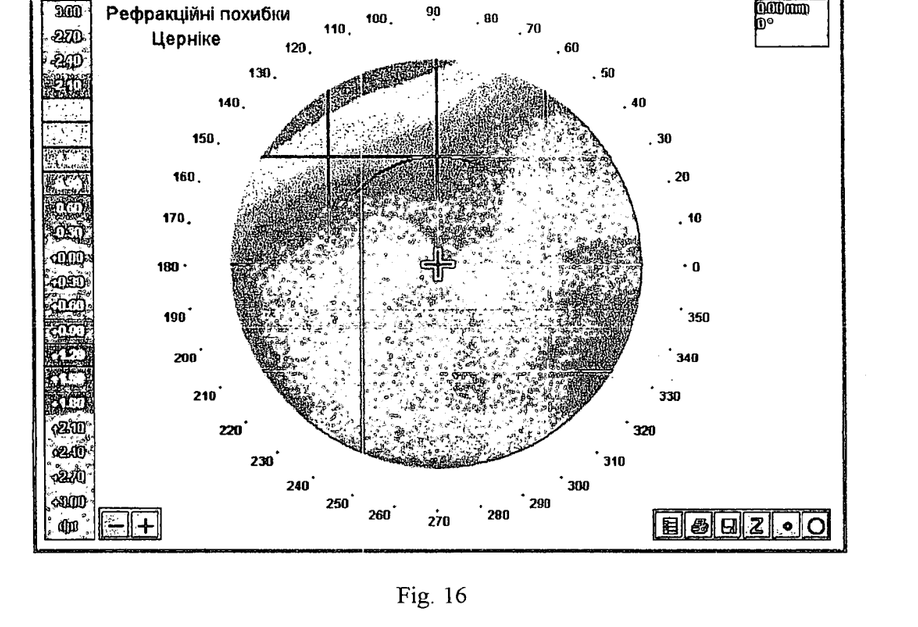
FIG. 16. Map of refraction errors, reconstructed by means of the least squares method using Zernike polynomials.
Figure 17:
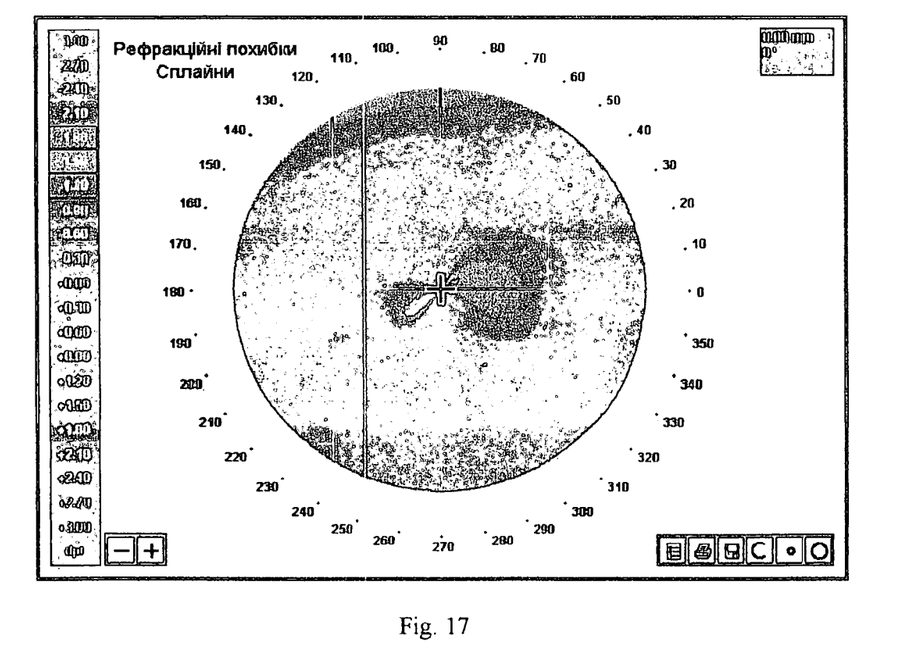
FIG. 17. Map of refraction errors, reconstructed when using the wave front approximation with the bicubic splines.

The information on the wave front aberrations can be converted into more easily perceptible information on the refraction errors. Examples of the information presented in the form of the two-dimensional color-coded maps are shown in FIGS. 16 and 17. In FIG. 16, the map is reconstructed as a result of wave front approximation using Zernike polynomials by means of the least squares method, and in FIG. 17, the map is reconstructed from the same primary measurement data but is the result of spline approximation. Comparing said maps makes it obvious that in the first case, the very important information on keratoconus is missing, but is clearly seen in FIG. 17 in the left lower quadrant. This example proves evident advantages of the use of the proposed method for measurement of wave aberrations of the eye.

The invention claimed is:

1. A method for measuring the wave aberrations of the eye, based on probing the eye with a narrow laser beam, detection of the radiation scattered by the retina, measurement of the wave front tilt in the form of the first partial derivatives along the coordinates in a discrete set of pupil points with known coordinates, approximation of the wave front in the form of functions of pupil coordinates using data from the detection of radiation scattered by the retina, and calculation of wave aberrations of the eye as deformations of the approximated wave front, characterized in that the partial derivatives at any pupil point are determined by means of spline approximation using the values in a discrete set of points, where the wave front tilts are measured, that are located along concentric circles with a common center which coincides with the center of coordinates, wherein the approximation of partial derivatives at the beginning is performed along each concentric circle and then along radii to the pupil points and the wave front is reconstructed by means of the numerical integration.

2. A method according to claim 1, wherein the wave front reconstructed by means of the numerical integration is along the radii to the pupil points with the initial point of integration located in the center of the pupil, where identical initial values of the integral are taken for all radii.

3. A method according to claim 2, characterized in that the numerical integration is performed in accordance with the formula:

$$W(P, \Phi) = W(0, \Phi) + \int_0^P \frac{\partial W(\rho, \Phi)}{\partial \rho} d\rho,$$

where $W(\rho,\phi)$ is the wave front function, $\rho$—the coordinate along the radius, $\phi$—the coordinate along the angle, $(P,\Phi)$ are the coordinates of arbitrary pupil point, and $$\int_0^P \frac{\partial W(\rho, \Phi)}{\partial \rho} d\rho \approx \sum_{i=1}^N \frac{\partial W\left(\frac{\rho_{i-1} + \rho_i}{2}, \Phi\right)}{\partial \rho} (\rho_i - \rho_{i-1}),$$

the interval [0,P] being divided into N partial portions $[\rho_i-1, \rho_i]$, so that $i=\overline{(1,N)}$.

4. A method according to claim 1, characterized in that the spline approximation along each coordinate is performed in accordance with the formula:

$$S(x) = \frac{(x_{i+1} - x)^2[2(x - x_i) + (x_{i+1} - x_i)]}{(x_{i+1} - x_i)^3} S(x_i) +$$
$$\frac{(x - x_i)^2[2(x_{i+1} - x) + (x_{i+1} - x_i)]}{(x_{i+1} - x_i)^3} S(x_{i+1}) +$$
$$\frac{(x_{i+1} - x)^2(x - x_i)}{(x_{i+1} - x_i)^2} S'(x_i) - \frac{(x - x_i)^2(x_{i+1} - x)}{(x_{i+1} - x_i)^2} S'(x_{i+1}),$$

where S(x) is the interpolation cubic spline along the generalized coordinate x; $x_i$, $x_i+1$ are the coordinates of the pupil points i and (i+1) from their discrete set, at which the wave front tilt is measured having corresponding values $S(x_i)$, $S(x_i+1)$; and $S'(x_i)$, $S'(x_i1)$ are the values of the first derivative in the points $x_i$, $x_i+1$, which ensure continuity of the second derivative S''(x) in these points.

5. A method according to claim 4, characterized in that the calculation of wave aberrations is performed based on the wave front data reconstructed in the form of splines.

6. A method according to claim 1, characterized in that the calculation of wave aberrations is performed based on the wave front data reconstructed in the form of splines.

7. A method according to claim 1, characterized in that the reconstructed wave front is used for the purposes of vision correction.

8. A method according to claim 1, characterized in that one or both of the reconstructed wave front or the discrete set of pupil points is in a polar coordinate system.

9. A method for measuring the wave aberrations of the eye, based on probing the eye at a discrete set of pupil points with a narrow laser beam, detection of the radiation scattered by the retina, measurement of the wave front tilt values in the form of first partial derivatives along known coordinates of the discrete set of pupil points in a rectangular coordinate system, approximation of the wave front in the form of functions of pupil coordinates using data from the detection of radiation scattered by the retina, and calculation of wave aberrations of the eye as deformations of an approximated wave front, wherein the first partial derivatives at any pupil point are determined by means of spline approximation using the data for the discrete set of pupil points, where the wave front tilt values are measured, that are located along straight lines which are parallel to an axis in the rectangular coordinate system and the wave front is reconstructed by means of numerical integration.

10. A method according to claim 9, wherein an approximation of the partial derivatives is performed along each of the parallel straight lines, and then in orthogonal directions.

11. A method according to claim 9, wherein the spline approximation along each coordinate is performed in accordance with the formula:

$$S(x) = \frac{(x_{i+1} - x)^2[2(x - x_i) + (x_{i+1} - x_i)]}{(x_{i+1} - x_i)^3} S(x_i) +$$
$$\frac{(x - x_i)^2[2(x_{i+1} - x) + (x_{i+1} - x_i)]}{(x_{i+1} - x_i)^3} S(x_{i+1}) +$$

-continued $$\frac{(x_{i+1}-x)^2(x-x_i)}{(x_{i+1}-x_i)^2}S'(x_i) - \frac{(x-x_i)^2(x_{i+1}-x)}{(x_{i+1}-x_i)^2}S'(x_{i+1}),$$

where S(x) is the interpolation cubic spline along the generalized coordinate x; $x_i$, $x_i+1$ are the coordinates of the pupil points i and (i+1) from their discrete set, at which the wave front tilt is measured having corresponding values $S(x_i)$, $S(x_i+1)$; and $S'(x_i)$, $S'(x_i+1)$ are the values of the first derivative in the points $x_i$, $x_i+1$, which ensure continuity of the second derivative S"(x) in these points.

12. A method according to claim 11, wherein the calculation of wave aberrations is performed based on the wave front data reconstructed in the form of splines.

13. A method according to claim 9, wherein the calculation of wave aberrations is performed based on the wave front data reconstructed in the form of splines.

14. A method according to claim 9, wherein the reconstructed wave front is used for the purposes of vision correction.

* * * * *